United States Patent
Mayer

(12) 
(10) Patent No.: US 6,572,591 B2
(45) Date of Patent: *Jun. 3, 2003

(54) NEEDLELESS INJECTION SITE

(75) Inventor: Bruno Franz P. Mayer, Santa Ana, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/849,091

(22) Filed: May 4, 2001

(65) Prior Publication Data

US 2001/0016715 A1 Aug. 23, 2001

Related U.S. Application Data

(60) Continuation of application No. 09/226,664, filed on Jan. 8, 1999, now Pat. No. 6,261,268, which is a continuation of application No. 09/055,102, filed on Apr. 3, 1998, now Pat. No. 5,971,965, which is a continuation of application No. 08/550,748, filed on Oct. 31, 1995, now Pat. No. 5,788,675, which is a division of application No. 08/262,994, filed on Jun. 20, 1994, now Pat. No. 5,470,319.

(51) Int. Cl.$^7$ .................................................. A61M 5/00

(52) U.S. Cl. ...................... 604/249; 604/256; 604/905; 251/149.1

(58) Field of Search ................. 604/48, 167.01–167.04, 604/167.06, 245–249, 284, 523, 905; 251/164.01, 249, 149.1–149.3, 354; 137/15.01, 15.18, 15.23–15.24, 511, 843

(56) References Cited

U.S. PATENT DOCUMENTS

| | | | | |
|---|---|---|---|---|
| 3,977,555 A | 8/1976 | Larson | ......................... | 215/247 |
| 4,063,460 A | 12/1977 | Svensson | ..................... | 73/425.6 |
| 4,134,512 A | 1/1979 | Nugent | ........................ | 215/247 |
| 4,246,899 A | 1/1981 | Loseff | ......................... | 128/276 |
| 4,301,936 A | 11/1981 | Percarpio | ..................... | 215/247 |
| 4,338,764 A | 7/1982 | Percarpio | ..................... | 53/432 |
| 4,655,752 A | 4/1987 | Honkanen et al. | ........... | 604/256 |
| 4,838,855 A | 6/1989 | Lynn | ............................ | 604/49 |
| 4,842,591 A | 6/1989 | Luther | ......................... | 604/167 |

(List continued on next page.)

FOREIGN PATENT DOCUMENTS

| | | |
|---|---|---|
| CA | 2001732 | 4/1990 |
| DE | 3105437 A1 | 10/1982 |
| DE | 3105439 C2 | 6/1986 |
| EP | 0309771 A1 | 5/1989 |
| EP | 0544581 | 11/1992 |
| FR | 0544581 A1 | 11/1992 |
| WO | 93/05838 | 1/1993 |
| WO | 93/05839 | 1/1993 |
| WO | 93/11828 * | 6/1993 |
| WO | WO 9600107 | 1/1996 |
| WO | 97/21464 | 6/1997 |

OTHER PUBLICATIONS

"STAT–LINK" Universal Connector with Valve.Safe Tech Medical Products, Inc. 2 pages.

Primary Examiner—Brian I. Gasler
Assistant Examiner—Loan H. Thanh
(74) Attorney, Agent, or Firm—James J. Murtha

(57) ABSTRACT

A needleless injection site comprising a housing defining proximal and distal ends and including a reseal member disposed therein. The reseal member has an elastically openable and closable aperture formed therein, and normally resides within the housing in a closed position wherein the aperture is in a closed configuration. The reseal member is deformable such that the application of distally directed pressure thereto will cause the reseal member to distally advance within the housing to an open position wherein the aperture assumes an open configuration. The removal of the distally directed pressure from the reseal member will cause it to resiliently return to the closed position wherein the aperture assumes the closed configuration.

2 Claims, 5 Drawing Sheets

U.S. PATENT DOCUMENTS

| | | | |
|---|---|---|---|
| 4,874,377 A | 10/1989 | Newgard et al. | 604/167 |
| 4,909,798 A | 3/1990 | Fleischhacker et al. | 604/167 |
| 5,064,416 A * | 11/1991 | Newgard et al. | 251/149.1 |
| 5,100,394 A | 3/1992 | Dudar et al. | 604/283 |
| 5,122,123 A | 6/1992 | Vaillancourt | 604/192 |
| 5,122,129 A | 6/1992 | Olson et al. | 604/905 |
| 5,135,489 A | 8/1992 | Jepson et al. | 604/48 |
| 5,154,703 A | 10/1992 | Bonaldo | 604/244 |
| 5,158,554 A | 10/1992 | Jepson et al. | 604/283 |
| 5,171,234 A | 12/1992 | Jepson et al. | 604/283 |
| 5,188,620 A | 2/1993 | Jepson et al. | 604/283 |
| 5,201,725 A | 4/1993 | Kling | 604/284 |
| 5,203,775 A | 4/1993 | Frank et al. | 604/256 |
| 5,207,661 A | 5/1993 | Repschlager | 604/317 |
| 5,215,538 A | 6/1993 | Larkin | 251/149.1 |
| 5,234,413 A | 8/1993 | Wonder et al. | 604/248 |
| 5,242,425 A | 9/1993 | White et al. | 604/256 |
| 5,242,432 A | 9/1993 | DeFrank | 604/284 |
| 5,250,033 A | 10/1993 | Evans et al. | 604/160 |
| 5,269,771 A | 12/1993 | Thomas et al. | 604/213 |
| 5,273,533 A | 12/1993 | Bonaldo | 604/83 |
| 5,273,545 A | 12/1993 | Hunt et al. | 604/167 |
| 5,286,453 A | 2/1994 | Pope | 422/100 |
| 5,324,256 A | 6/1994 | Lynn et al. | 604/49 |
| 5,330,435 A | 7/1994 | Vaillancourt | 604/167 |
| 5,336,192 A | 8/1994 | Palestrant | 604/167 |
| 5,360,012 A | 11/1994 | Ebara et al. | 128/764 |
| 5,360,413 A | 11/1994 | Leason et al. | 604/256 |
| 5,380,306 A | 1/1995 | Brinon | 604/244 |
| 5,401,245 A | 3/1995 | Haining | 604/86 |
| 5,439,451 A | 8/1995 | Collinson et al. | 604/247 |
| 5,470,319 A * | 11/1995 | Mayer | 251/149.1 |
| 5,474,544 A | 12/1995 | Lynn | 604/283 |
| 5,487,728 A | 1/1996 | Vaillancourt | 604/86 |
| 5,501,426 A | 3/1996 | Atkinson et al. | 251/149.1 |
| 5,509,912 A | 4/1996 | Vaillancourt et al. | 604/283 |
| 5,514,116 A | 5/1996 | Vaillancourt et al. | 604/283 |
| 5,520,665 A | 5/1996 | Fleetwood | 604/283 |
| 5,520,666 A | 5/1996 | Choudhury et al. | 604/283 |
| 5,549,566 A | 8/1996 | Elias et al. | 604/167 |
| 5,549,577 A | 8/1996 | Siegel et al. | 604/256 |
| 5,578,059 A | 11/1996 | Patzer | 604/249 |
| 5,616,129 A | 4/1997 | Mayer | 604/167 |
| 5,616,130 A | 4/1997 | Mayer | 604/167 |
| 5,620,434 A | 4/1997 | Brony | 604/406 |
| 5,638,663 A | 6/1997 | Lopez | 604/249 |
| 5,669,891 A | 9/1997 | Vaillancourt | 604/283 |
| 5,685,866 A | 11/1997 | Lopez et al. | 604/249 |
| 5,688,254 A | 11/1997 | Lopez et al. | 604/283 |
| 5,690,612 A | 11/1997 | Lopez et al. | 604/93 |
| 5,694,686 A | 12/1997 | Lopez | 29/890.126 |
| 5,695,466 A | 12/1997 | Lopez et al. | 604/93 |
| 5,699,821 A | 12/1997 | Paradis | 137/1 |
| 5,700,248 A | 12/1997 | Lopez | 604/249 |

\* cited by examiner

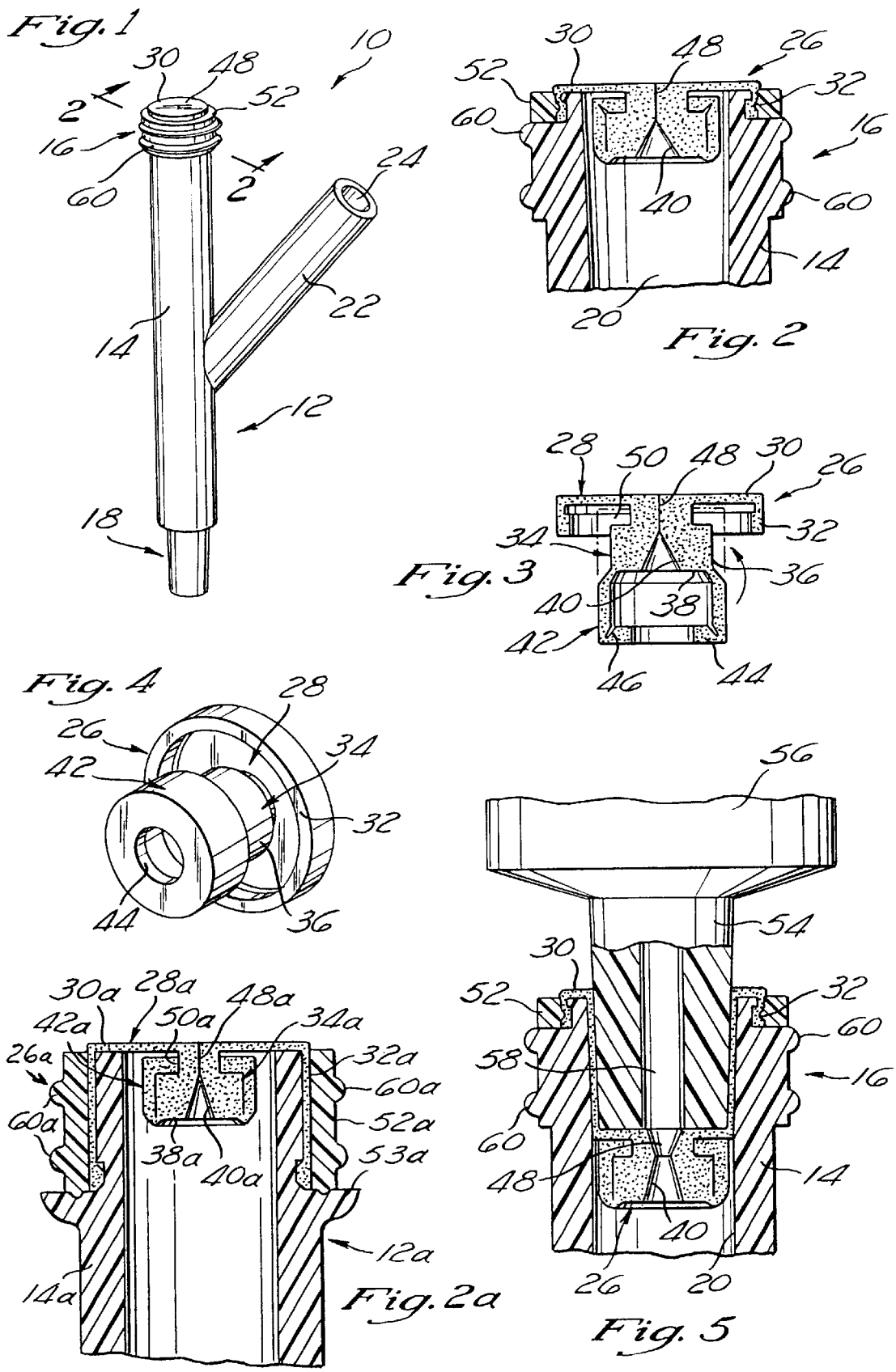

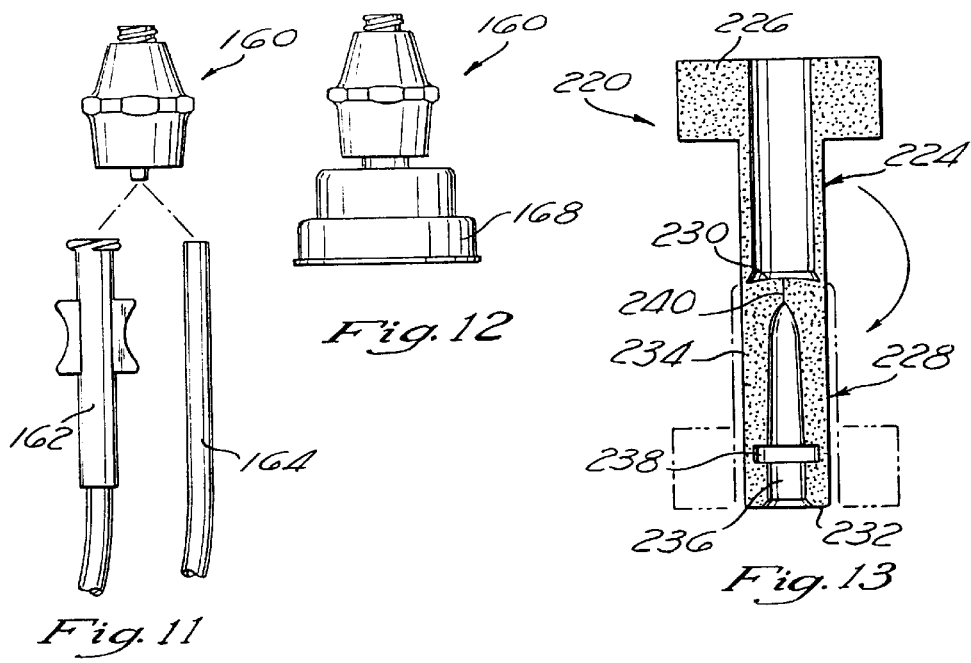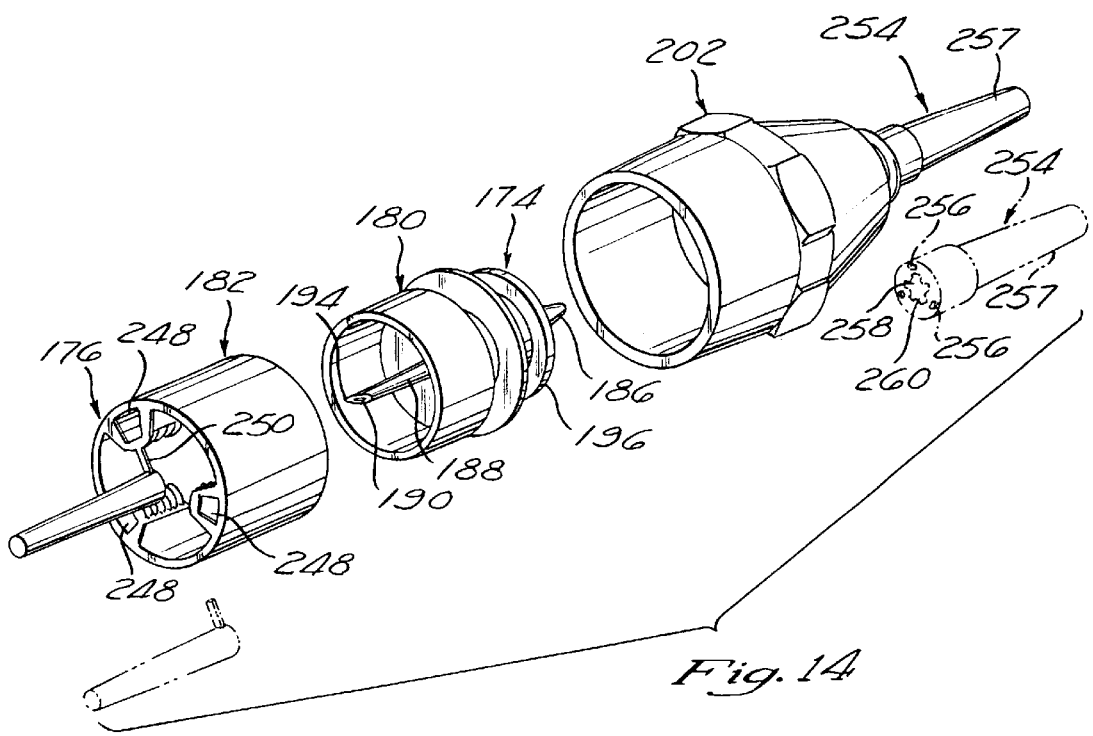

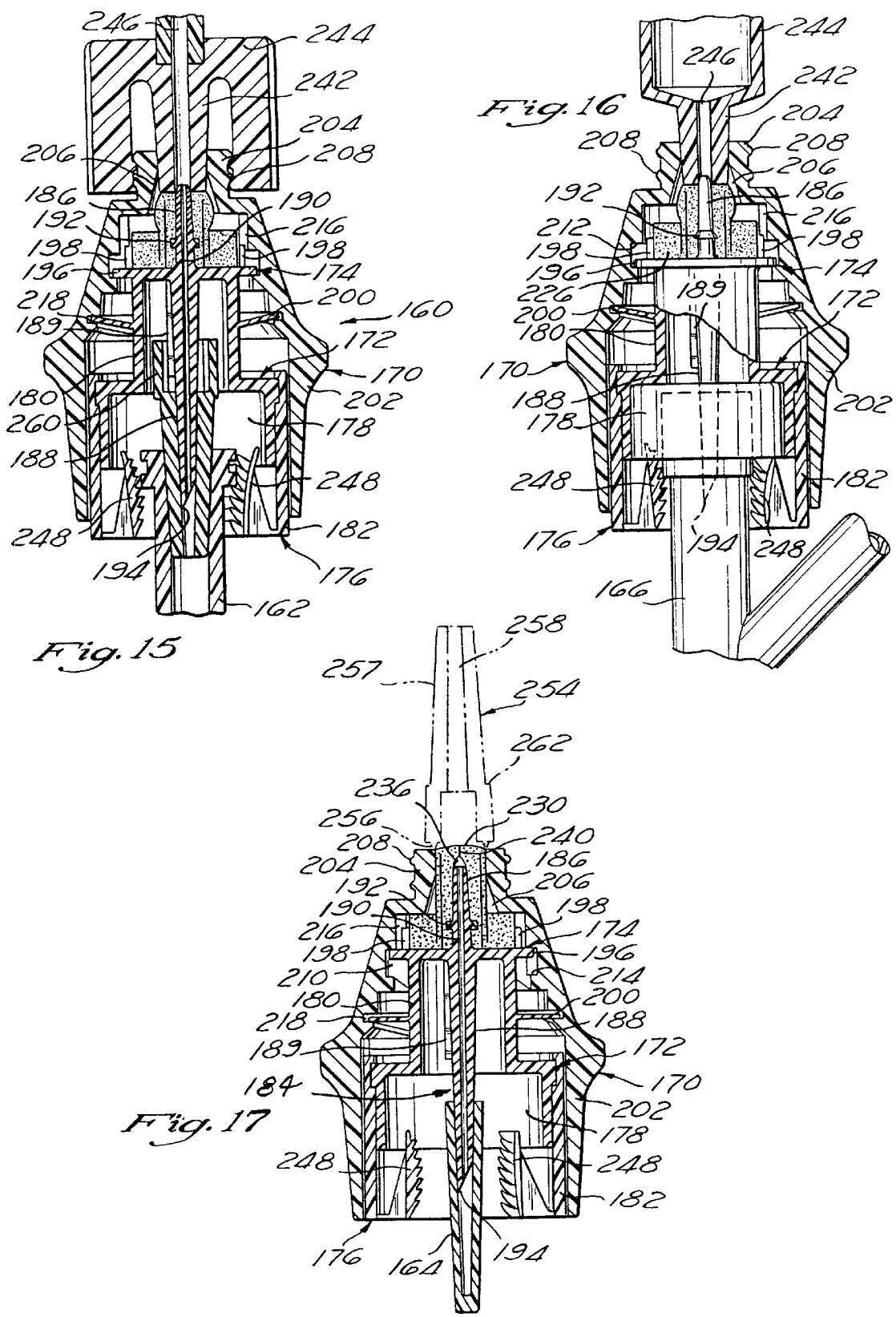

NEEDLELESS INJECTION SITE

This application is a continuation of Ser. No. 09/226,664 filed Jan. 8, 1999, now U.S. Pat. No. 6,261,268, which is a continuation of Ser. No. 09/055,102 filed Apr. 3, 1998, now U.S. Pat. No. 5,971,965, which is a continuation of Ser. No. 08/550,748 filed Oct. 31, 1995, U.S. Pat. No. 5,788,675, which is a divisional of Ser. No. 08/262,994 filed Jun. 20, 1994, now U.S. Pat. No. 5,470,319.

FIELD OF THE INVENTION

The present invention relates generally to the medical arts, and more particularly to a needleless injection site for use in relation to intravenous infusions.

BACKGROUND OF THE INVENTION

It is common medical practice to intravenously infuse various fluids into the blood vessels of a patient. Such infusion is typically accomplished by the insertion of a hollow introducer needle into a target blood vessel. The introducer needle is fluidly connected to one end of an elongate, flexible tube, the opposite end of which is fluidly connected to a solution bag. The solution bag itself is typically suspended above the patient so as to allow the fluid to flow downwardly through the tubing and into the patient's blood vessel via the introducer needle which remains operatively positioned therewithin. The fluid tube and solution bag are connected to each other via a metering apparatus which controls the infusion rate of fluid from the bag into the tube.

In many intravenous infusion assemblies, an injection site is fluidly coupled within the tubing intermediate the introducer needle and the solution bag. The injection site typically has a Y-shaped configuration and comprises a tubular main body portion having a tubular side arm portion in fluid communication therewith. The distal end of the side arm portion is fluidly connected to the solution bag via an upper segment of the tubing, with the bottom end of the main body portion being fluidly connected to the introducer needle via a lower segment of the tubing. The top end of the main body portion is itself covered by a diaphragm which is typically fabricated from rubber or a similar resilient material.

The inclusion of the injection site within the tubing allows various medications to be selectively infused into the blood vessel of the patient by the addition thereof to the solution flowing from the solution bag into the blood vessel via the upper tubing segment, injection site, lower tubing segment and introducer needle. This supplemental infusion is typically accomplished through the utilization of a conventional syringe, the needle of which pierces and is extended through the diaphragm disposed on the top end of the main body portion of the injection site. Subsequent to the expulsion of the medication from within the syringe and into the flowing solution, the needle is retracted out of the main body portion of the injection site, with the aperture created in the diaphragm due to the passage of the needle therethrough being substantially closed upon such retraction due to the resiliency of the diaphragm. As will be recognized, the incorporation of the injection site within the tubing allows various medications to be intravenously administered to the patient through the existing infusion site within the blood vessel, thus eliminating the need to subject the patient to additional needle sticks.

Though providing certain benefits to the patient, the injection sites constructed in accordance with the prior art possess certain deficiencies which detract from their overall utility. As previously explained, the use of such injection sites typically requires that the needle of a conventional syringe be extended through (i.e., puncture) the diaphragm attached to the top end of the main body portion of the injection site. However, the necessity of having to utilize a syringe with a needle to facilitate the introduction of the medication into the solution flow is undesirable due to the risk of inadvertent needle sticks. In recognition of this deficiency, there has also been developed in the prior art needleless injection sites which incorporate a diaphragm adapted to assume open and closed configurations without having a needle inserted thereinto. Though these needleless injection sites eliminate the need of having to puncture the diaphragm with a needle, they also possess certain deficiencies which detract from their overall utility. Foremost of these deficiencies is the difficulty associated with disinfecting the injection site, and in particular the diaphragm thereof, subsequent to medication being infused thereinto. In this respect, after each use of the injection site the diaphragm must be cleaned, with such cleaning typically being accomplished through the application of alcohol or a similar disinfecting substance thereto. However, due to the configuration of the diaphragm, complete and effective disinfection thereof is often difficult to achieve, thus increasing the risk of the introduction of contaminates into the solution stream upon subsequent uses of the injection site. The present invention is adapted to overcome these and other deficiencies associated with prior art injection sites.

SUMMARY OF THE INVENTION

In accordance with a first embodiment of the present invention, there is provided a needleless injection site comprising a housing. The housing itself comprises a main body portion defining proximal and distal ends, and a bore extending axially therethrough. The housing further comprises a tubular side arm portion which is in fluid communication with the main body portion.

Attached to the proximal end of the main body portion is a reseal member which extends into the bore and includes an elastically openable and closable aperture formed therein. The reseal member normally resides in a closed position wherein the aperture is in a closed configuration. In the first embodiment, the reseal member is deformable such that the application of distally pressure thereto will cause it to distally advance within the bore to an open position wherein the aperture assumes an open configuration. Conversely, the removal of the distally directed pressure from the reseal member will cause it to resiliently return to the closed position wherein the aperture assumes the closed configuration.

The reseal member is preferably fabricated from silicone and comprises a circularly configured proximal portion which defines a top surface and has a flange formed about the periphery thereof for attaching the reseal member to the main body portion of the housing. The reseal member further comprises a cylindrically configured central portion which defines a side surface and a bottom surface having a conically shaped notch formed therein. The aperture extends from the top surface of the proximal portion to the apex of the notch. In addition to the proximal and central portions, the reseal member includes a tubular distal portion which is invertible and adapted to overlap the side surface of the central portion and apply a radially inward biasing force thereto when inverted which maintains the aperture in the closed configuration when no distally directed pressure is applied to the top surface of the proximal portion.

The injection site of the first embodiment further comprises a lock ring for securing the reseal member to the proximal end of the main body portion. In this respect, the flange of the reseal member is rigidly captured between the main body portion and the lock ring. Additionally, formed on the outer surface of the main body portion adjacent the proximal end thereof are Luer threads.

In accordance with a second embodiment of the present invention, there is provided a needleless injection site comprising a housing which also comprises a main body portion defining proximal and distal ends and a bore extending axially therethrough. Formed on the proximal end of the main body portion and extending axially therefrom is an elongate dilator projection. The dilator projection defines a longitudinally extending fluid passage which is in fluid communication with the bore. Attached to the proximal end of the main body portion is a connector cap which defines a central opening into which the dilator projection extends. The housing further comprises a tubular side arm portion which is in fluid communication with the main body portion.

Disposed within the opening of the connector cap is a reseal member which has an elastically openable and closable aperture formed therein, and normally resides in a closed position wherein the aperture is in a closed configuration. The dilator projection of the housing extends into the reseal member. The reseal member is deformable such that the application of distally directed pressure thereto will cause it to distally advance within the opening to an open position wherein the aperture is forced over a portion of the dilator projection. Conversely, the removal of the distally directed pressure from the reseal member will cause it to resiliently return to the closed position wherein the aperture assumes the closed configuration.

In the second embodiment, the reseal member is attached to the connector cap and comprises a circularly configured proximal portion which defines a top surface and has a flange formed about the periphery thereof for attaching the reseal member to the connector cap. The reseal member further comprises a cylindrically configured central portion which defines a side surface and a bottom surface having an elongate, generally concave recess formed herein which is sized and configured to receive the dilator projection. The aperture extends from the top surface of the proximal portion to the apex of the recess. In addition to the proximal and central portions, the reseal member includes a tubular distal portion which is invertible and adapted to overlap the side surface of the central portion and apply a radially inward biasing force thereto when inverted which maintains the aperture in the closed configuration when no distally directed pressure is applied to the top surface of the proximal portion. Like the reseal member previously described in relation to the first embodiment, the reseal member constructed in accordance with the second embodiment is preferably fabricated from silicone. Additionally, the reseal member is preferably cooperatively engaged to the dilator projection and disposed in abutting contact with the proximal end of the main body portion.

The connector cap of the housing includes Luer threads formed on the outer surface thereof adjacent the central opening. Additionally, the main body portion of the housing normally resides in a first position within the connector cap, and is adapted to move distally relative the connector cap to a second position therewithin when distally directed pressure is applied to the reseal member. The removal of the distally directed pressure from the reseal member causes the main body portion to resiliently return to the first position. The main body portion preferably includes a leaf spring molded thereon which is cooperatively engaged to the connector cap and adapted to bias the main body portion to the first position.

In accordance with a third embodiment of the present invention, there is provided a needleless injection site comprising a housing. The housing itself comprises an adapter member defining proximal and distal ends, and an interior chamber. Formed on the proximal end of the adapter member is an elongate dilator projection which defines a proximal portion extending axially from the proximal end, a distal portion extending axially into the interior chamber, and a longitudinally extending fluid passage in fluid communication with the interior chamber. Attached to the adapter member is a connector cap which defines a central opening. The adapter member is disposed within the connector cap, with the proximal portion of the dilator projection extending into the opening thereof.

Disposed within the opening is a reseal member which has an elastically openable and closeable aperture formed therein, and normally resides in the closed position wherein the aperture is in a closed configuration. The proximal portion of the dilator projection extends into the reseal member. The reseal member is deformable such that the application of distally directed pressure thereto will cause it to distally advance within the opening to an open position wherein the aperture is forced over the proximal portion of the dilator projection. Conversely, the removal of the distally directed pressure from the reseal member will cause it to resiliently return to the closed position wherein the aperture assumes the closed configuration. The reseal member, which is also preferably fabricated from silicone, comprises a tubular proximal portion and a cylindrically configured distal portion defining top, bottom and side surfaces, and including an elongate, generally concave recess formed in the bottom surface thereof which is sized and configured to receive the proximal portion of the dilator projection. The aperture extends from the top surface of the distal portion to the apex of the recess. The proximal portion is invertible and adapted to overlap the side surface of the distal portion and apply a radially inward biasing force thereto when inverted which maintains the aperture in the closed configuration when no distally directed pressure is applied to the top surface of the distal portion. The reseal member is preferably cooperatively engaged to the proximal portion of the dilator projection and disposed in abutting contact with the proximal end of the adapter member.

The connector cap of the housing constructed in accordance with the third embodiment also includes Luer threads formed on the outer surface thereof adjacent the central opening. Additionally, the adapter member normally resides in a first position within the connector cap, and is adapted to move distally relative the connector cap to a second position therewithin when distally directed pressure is applied to the reseal member. When the distally directed pressure is removed from the reseal member, the adapter member resiliently returns to the first position. The adapter member preferably includes a leaf spring molded thereon which is cooperatively engaged to the connector cap and adapted to bias the adapter member to the first position.

In the third embodiment, the distal portion of the dilator projection has a tapered outer surface for facilitating the connection of the adapter member and hence the housing to a tubular fluid line. In particular, the housing is connected to the fluid line via the insertion of the distal portion of the dilator projection into the lumen of the fluid line, with the distal portion being frictionally retained within the lumen subsequent to being inserted thereinto.

The adapter member further comprises a tubular adapter sleeve which is slidably extensible over and frictionally maintainable on the distal portion of the dilator projection for facilitating the connection of the housing to a Luer connector. The housing is connected to the Luer connector via the insertion of the adapter sleeve into the lumen of the Luer connector. The distal portion of the dilator projection preferably has a tapered outer surface, with the adapter sleeve preferably having a tapered bore extending longitudinally therethrough which is complimentary to the outer surface of the distal portion of the dilator projection, thus facilitating the frictional retention of the adapter sleeve thereon. Additionally, the distal portion of the dilator projection preferably includes an elongate rib formed on the outer surface thereof, with the bore of the adapter sleeve defining an elongate slot therewithin which is sized and configured to receive the rib when the adapter sleeve is slidably advanced over the distal portion of the dilator projection. The receipt of the rib into the slot is operable to prevent the rotation of the adapter sleeve upon the distal portion of the dilator projection. Further, the adapter sleeve preferably has a tapered outer surface for frictionally retaining the adapter sleeve within the lumen of the Luer connector subsequent to being inserted thereinto.

The adapter member of the housing further defines a tubular lock region within the distal end thereof which is configured to engage the Luer threads of the Luer connector when the adapter sleeve is inserted into the lumen thereof. The lock region preferably defines a plurality of Luer thread pitch barbs therewithin which engage the Luer threads. The lock region of the adapter member is also used to facilitate the connection of the housing to a Y-injection site. In particular, the housing is connected to the Y-injection site via the insertion of the Y-injection site into the lock region of the adapter member, and the extension of the distal portion of the dilator projection thereinto. In the third embodiment, the adapter member preferably comprises an upper section defines the dilator projection, and a lower section which is rigidly attached to the upper section and defines the lock region, with the upper and lower sections defining the interior chamber when attached to each other.

Further in accordance with the present invention, there is provided a method of fabricating a reseal member for use in a needleless injection site. The method comprises the step of molding the reseal member to include a circularly configured proximal portion, a cylindrically configured central portion having an opening formed in the bottom surface thereof, an aperture extending from the top surface of the proximal portion to the opening, and a tubular distal portion. The method further comprises the step of inverting the distal portion in a manner causing it to overlap the side surface of the central portion and apply a radially inward biasing force thereto which maintains the aperture in a closed configuration. The method may further comprise the step of forming a flange about the periphery of the proximal portion. The opening formed within the central portion may comprise a conically-shaped notch, with the aperture extending from the top surface of the proximal portion to the apex of the notch. Alternatively, the opening may comprise an elongate, concave recess, with the aperture extending from the top surface of the proximal portion to the apex of the recess.

There is also provided a method of fabricating a reseal member for use in a needleless injection site which comprises the step of molding the reseal member to include a tubular proximal portion, a cylindrically configured distal portion having a concave recess formed in the bottom surface thereof, and an aperture extending from the top surface of the distal portion to the apex of the recess. The method further includes the step of inverting the proximal portion in a manner causing it to overlap the side surface of the distal-portion and apply a radially inward biasing force thereto which maintains the aperture in a closed configuration.

BRIEF DESCRIPTION OF THE DRAWINGS

These, as well as other features of the present invention, will become more apparent upon reference to the drawings wherein:

FIG. 1 is a perspective view of a needleless injection site constructed in accordance with a first embodiment of the present invention;

FIG. 2 is a cross-sectional view taken along line 2—2 of FIG. 1;

FIG. 2a is a cross-sectional view of a reseal member adapted to be attached to a y-shaped housing.

FIG. 3 is a cross-sectional view of the reseal member incorporated into the needleless site shown in FIG. 1;

FIG. 4 is a perspective view of the reseal member shown in FIG. 3;

FIG. 5 is a cross-sectional view illustrating the manner in which the reseal member is deformable from a closed to an open position;

FIG. 11 is a side elevational view of a needleless injection site constructed in accordance with a third embodiment of the present invention, and further illustrating a Luer connector and a tubing end to which it may be connected;

FIG. 12 is a side elevational view of the needleless injection site constructed in accordance with the third embodiment of the present invention as connected to a bottle;

FIG. 13 is a cross-sectional view of the reseal member incorporated into the needleless injection site shown in FIGS. 11 and 12;

FIG. 14 is an exploded perspective view of the needleless injection site constructed in accordance with the third embodiment of the present invention;

FIG. 15 is a cross-sectional view of the needleless injection site shown in FIGS. 11 and 12 as connected to a Luer connector, with the reseal member thereof being deformed into an open position;

FIG. 16 is a cross-sectional view of the needleless injection site shown in FIGS. 11 and 12 as connected to a Y-injection site, with the reseal member thereof being deformed into an open position; and FIG. 17 is a cross-sectional view of the needleless injection site shown in FIGS. 11 and 12 as connected to a tubular fluid line, with the reseal member thereof being in a closed position.

DETAILED DESCRIPTION OF THE PREFERRED EMBODIMENT

Figure 6:
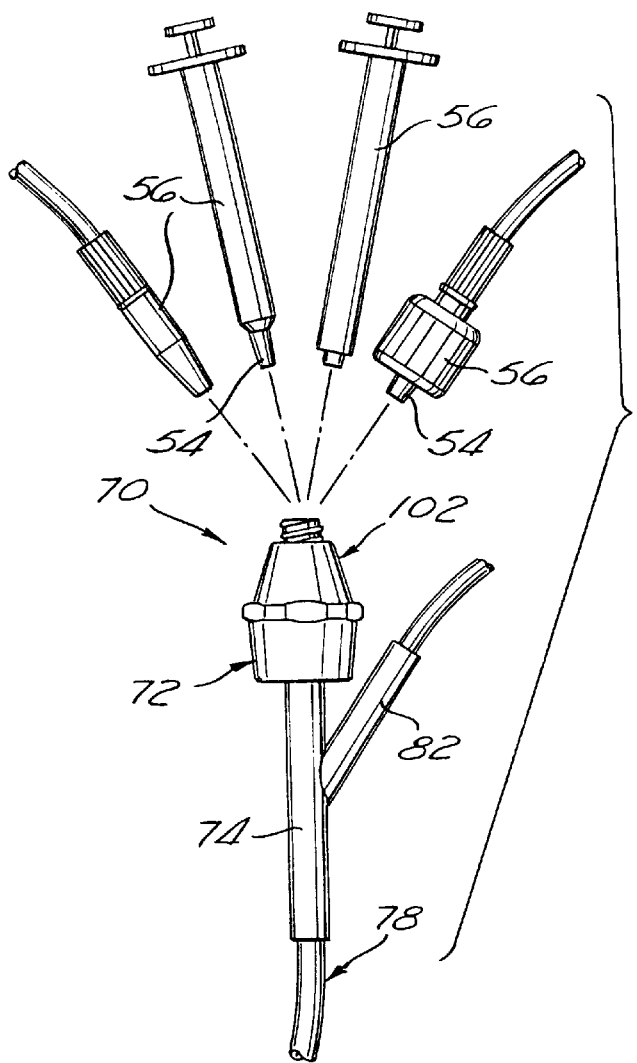
FIG. 6 is a side elevational view of a needleless injection site constructed in accordance with a second embodiment of the present invention, and further illustrating various devices which may be connected thereto.

Referring now to the drawings wherein the showings are for purposes of illustrating preferred embodiments of the present invention only, and not for purposes of limiting the same, FIG. 1 perspectively illustrates a needleless injection site 10 constructed in accordance with a first embodiment of the present invention. In the first embodiment, the injection site 10 comprises a Y-shaped housing 12. The housing 12 itself comprises a main body portion 14 which defines a proximal end 16, a distal end 18 and a bore 20 extending axially therethrough. The housing 12 further comprises a tubular side arm 22 portion which extends angularly from the main body portion 14 and defines a bore 24 in fluid communication with the bore 20 of the main body portion 14. In typical intravenous infusion applications, the side arm portion 22 is fluidly connected to a suspended solution bag via an upper segment of tubular fluid line. The distal end 18 of the main body portion 14 is itself fluidly connected to a hollow introducer needle via an elongate lower segment of tubular fluid line, thus allowing the solution to flow from the bag into a target blood vessel via the upper tubing segment, injection site 10, lower tubing segment and introducer needle.

Referring now to FIGS. 2–5, attached to the proximal end 16 of the main body portion 14 is a reseal member 26 which is fabricated from a resilient material and extends into the bore 20. As best seen in FIGS. 3 and 4, the reseal member 26 comprises a circularly configured proximal portion 28 which defines a top surface 30 and includes a flange 32 formed about the periphery thereof. The reseal member 26 further comprises a cylindrically configured central portion 34 which defines a side surface 36 and a bottom surface 38 having a conically shaped notch 40 formed in the center thereof. In addition to the proximal and central portions 28, 34, the reseal member 26 comprises a tubular distal portion 42 which includes, an annular lip 44 formed about the inner surface thereof. The distal portion 42 is preferably formed in a manner wherein a slit 46 is disposed in the corner region defined between the lip 44 and the remainder of the distal portion 42. Extending from the top surface 30 of the proximal portion 28 to the apex of the notch 40 is an aperture 48 which is elastically openable and closable. In the injection site 10, the reseal member 26 normally resides in a closed position wherein the aperture 48 is in a closed configuration.

To maintain the aperture 48 in the closed configuration, the distal portion 42 of the reseal member 26 is formed so as to be invertible in relation to the remainder thereof. As best seen in FIGS. 2 and 5, the distal portion 42, when inverted, is adapted to overlap the side surface 36 of the central portion 34 and apply a radially inward biasing force thereto which maintains the aperture in the closed configuration. Such inversion is accomplished by initially turning the lip 44 outwardly, thus causing the same to extend radially outward with respect to the remainder of the distal portion 42. The outward turning of the lip 44 is aided by the inclusion of the slit 46 within the distal portion 42. Thereafter, the distal portion 42 is rolled toward the proximal portion 28, with the lip 44 being inserted into the annular channel 50 defined between the proximal and central portions 28, 34. When the distal portion 42 is properly inverted, the reseal member 26 assumes the configuration shown in FIG. 2. For ease of manufacture, the reseal member 26 is molded in the form shown in FIGS. 3 and 4, with the distal portion 42 thereof being inverted in the aforementioned manner prior to the attachment of the reseal member 26 to the proximal end 16 of the main body portion 14. As previously explained, due to the resiliency of the material from which the reseal member 26 is fabricated, the inversion of the distal portion 42 facilitates the application of a radially inward biasing force to the central portion 34, thus maintaining the aperture 48 in the closed configuration.

In the injection site 10, the housing 12 further comprises an annular lock ring 52 for securing the reseal member 26 to the proximal end 16 of the main body portion 14. In particular, the attachment of the reseal member 26 to the main body portion 14 is accomplished by the rigid capture of the flange 32 between the main body portion 14 and lock ring 52 which is itself attached to the main body portion 14 via a sonic bonding process. When attached to the main body portion 14 via the lock ring 52, the central portion 34 of the reseal member 26 (which is covered by the inverted distal portion 42) resides within the bore 20.

The reseal member 26, due to its construction, is deformable such that the application of distally directed pressure thereto will cause it to distally advance within the bore 20 to an open position wherein the aperture 48 assumes an open configuration (as shown in FIG. 5). Conversely, the removal of the distally directed pressure from the reseal member 26 will cause it to resiliently return to the closed position wherein the aperture 48 assumes the closed configuration. In particular, when the reseal member 26 is in the closed position (as shown in FIG. 2), the top surface 30 of the proximal portion 28 extends over (i.e., covers) the proximal end 16 of the main 20 body portion 14, with the aperture 48 being in the closed configuration due to the radially inward biasing force applied to the central portion 34 by the inverted distal portion 42. When the tip 54 of an introducer device 56 is used to apply distally directed pressure to the top surface 30 of the proximal portion 28, such pressure application causes the reseal member 26 (with the exception of the flange 32) to distally advance within the bore 20 (as shown in FIG. 5). Due to the rigid attachment of the flange 32 to the proximal end 16 of the main body portion 14 via the lock ring 52, the advancement of the reseal member 26 distally within the bore 20 causes the aperture 48 to assume the open configuration, which allows fluid to flow from the outlet passage 58 of the introducer device 56 into the bore 20 via the pathway defined by the open aperture 48 and notch 40. Additionally, due to the resiliency of the reseal member 26, the removal of the introducer device 56 from within the injection site 10 allows it to resiliently return to its closed position (shown in FIG. 10), thus causing the aperture 48 to once again assume the closed configuration. In this respect, when no distally directed pressure is applied to the top surface 30 of the proximal portion 28, the aperture 48 is maintained in the closed configuration by the radially inward biasing force exerted on the central portion 34 by the inverted distal portion 42. The tip 54 of the introducer device 56 is preferably sized having an outer diameter dimension which is slightly less than the inner diameter dimension of the bore 20, thus allowing the stretched region of the proximal portion 28 to form a seal between the outer surface of the tip 54 and inner surface of the bore 20.

In the injection site 10, the reseal member 26 is preferably fabricated from silicone, though similar elastic materials such as rubber may be utilized as an alternative. Additionally, the outer surface of the main body portion 14 preferably includes Luer threads 60 formed thereon adjacent the proximal end 16 to allow introducer devices such as Luer connectors to be interfaced to the injection site 10. Advantageously, the uniform top surface 30 defined by the proximal portion 28 when the reseal member 26 is in the closed position allows for the quick and easy cleaning and disinfection thereof. Though the reseal member 26 has been described as being used in conjunction with the Y-shaped housing 12, it will be recognized that the reseal member 26 may also be used in association with a Luer connector, a conventional tubular fluid line or any other type of injection site.

Referring now to FIG. 2a, there is depicted a reseal member 26a which is adapted to be attached to the proximal end of an alternative Y-shaped housing 12a. The reseal member 26a is substantially identical to the reseal member 26 previously described and comprises a circularly configured proximal portion 28a which defines a top surface 30a and includes the flange 32a formed about the periphery thereof. The reseal member 26a further comprises a cylindrically configured central portion 34a which defines a bottom surface 38a having a conically shaped notch 40a formed in the center thereof and a side surface which is overlapped by an inverted, tubular distal portion 42a. Extending from the top surface 30a of the proximal portion 28a to the apex of the notch 40a is an aperture 48a which is elastically openable and closable. The only distinction between the reseal member 26a and the reseal member 26 is in the configuration of the flange 32a which is substantially longer than the flange 32 for reasons which will be discussed below.

The house 12a to which the reseal member 26a is attached is similar to the housing 12 previously described but does not include the Luer threads 60a formed on the outer surface on the main body portion 14a thereof. Rather, the proximal portion of the main body portion 14a of the housing 12a defines a generally smooth outer surface over which the flange 32a is extended. As an alternative to the lock ring 52 previously described, the housing 12a further comprises an annular lock ring 52a for securing the reseal member 26a to the proximal end of the main body portion 14a. In particular, the attachment of the reseal member 26a to the main body portion 14a is accomplished by the rigid capture of the flange 32a between the main body portion 14a and lock ring 52a which is itself attached to annular shoulder 53a formed about the outer surface of the main body portion 14a via a sonic bonding process. The outer surface of the lock ring 52a preferably includes Luer threads 60a formed thereon to allow introducer devices such as Luer connectors to be interfaced to the housing 12a.

Though not shown, it will be recognized that alternative means may be utilized to apply a radially inward biasing force to the central portion 34, 34a of the reseal member 26, 26a to maintain the aperture 48, 48a in the closed configuration. In this respect, the reseal member 26, 26a may be formed without the invertable distal portion 42, 42a, with the radially inward biasing force being applied to the central portion 34, 34a by an O-ring which is received into the annular channel 50, 50a defined between the proximal portion 28, 28a and central portion 34, 34a.

Referring now to FIGS. 6–10, illustrated is a needleless injection site 70 constructed in accordance with a second embodiment of the present invention. In the second embodiment, the injection site 70 preferably comprises a Y-shaped housing 72, though the housing 72 may alternatively have a straight configuration. The housing 72 itself comprises a main body portion 74 which defines a proximal end 76, a distal end 78 and a bore 80 extending axially therethrough. Extending angularly from the main body portion 74 is a tubular side arm portion 82 which is in fluid communication with the bore 80 of the main body portion 74. In typical intravenous infusion applications, the side arm portion 82 of the housing 72 is fluidly connected to a suspended solution bag via an upper segment of tubular fluid line. The distal end 78 of the main body portion 74 is itself fluidly connected to a hollow introducer needle via an elongate lower segment of tubular fluid line, thus allowing the solution to flow from the bag into a target blood vessel via the upper tubing segment, injection site 70, lower tubing segment and introducer needle.

Figure 7:
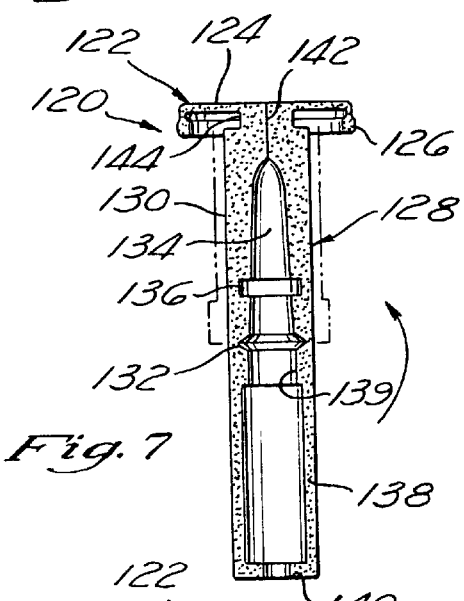
FIG. 7 is a cross-sectional view of the reseal member incorporated into the needleless injection site shown in FIG. 6.
Figure 8:
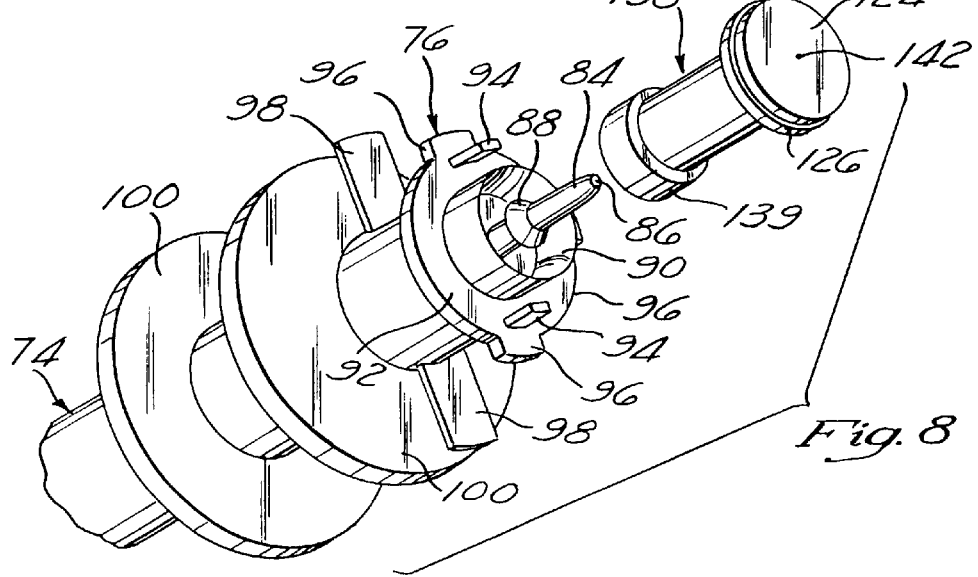
FIG. 8 is an exploded perspective view of the main body portion and reseal member of the needleless injection site shown in FIG. 6.
Figure 9:
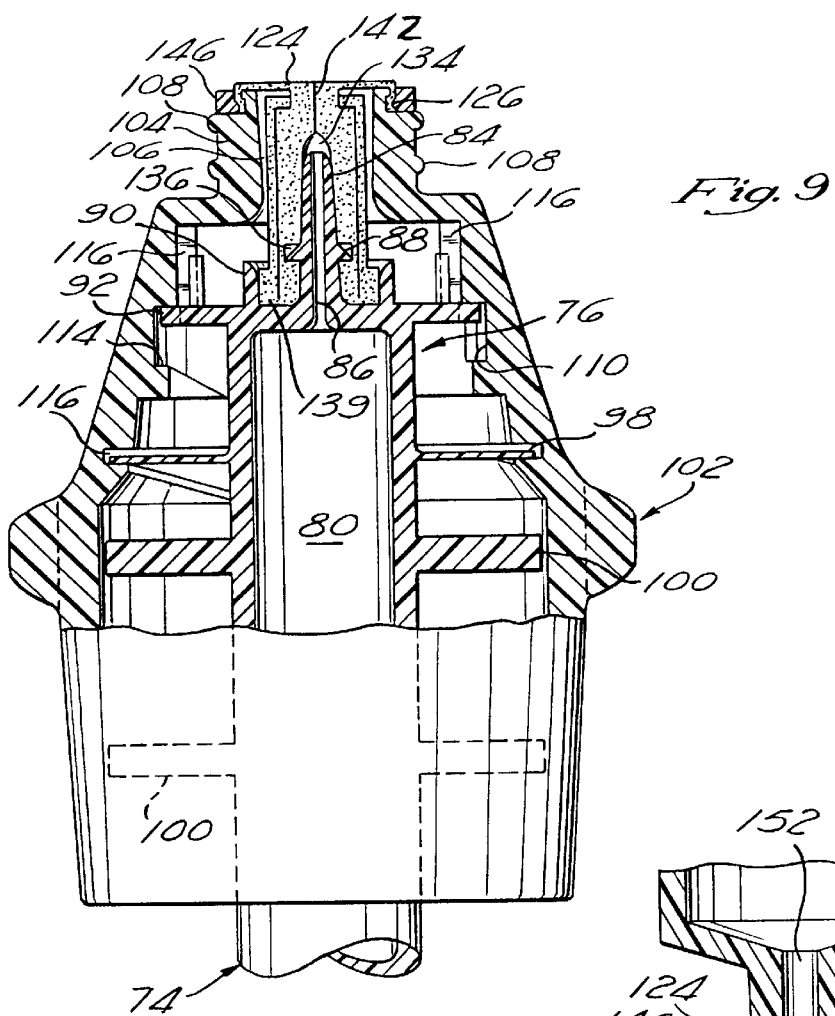
FIG. 9 is a partial cross-sectional view of the needleless injection site shown in FIG. 6, with the reseal member thereof being in a closed position.
Figure 10:
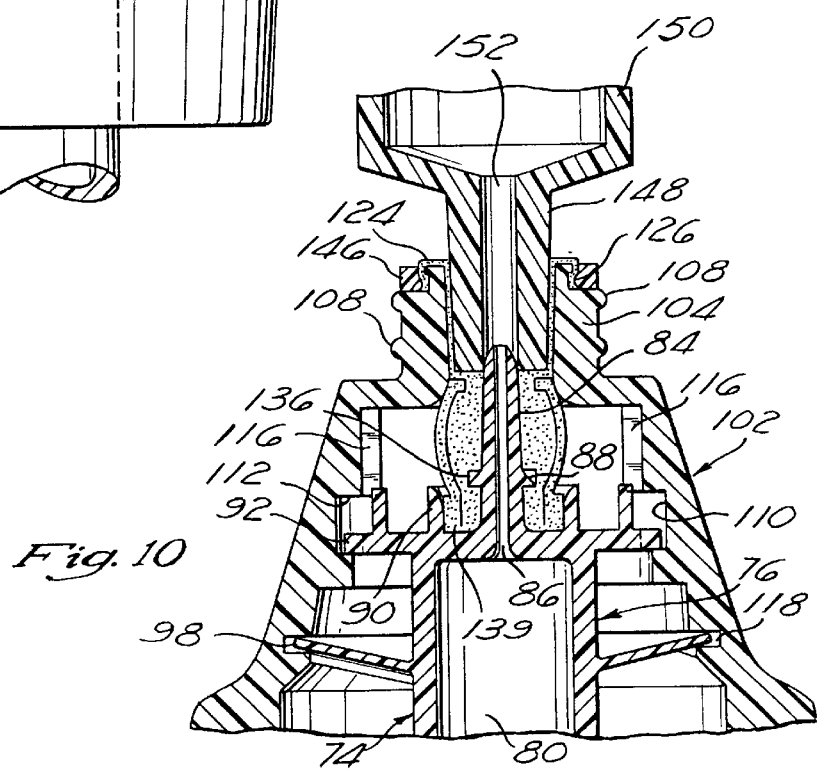
FIG. 10 is a partial cross-sectional view of the needleless injection site shown in FIG. 6, with the reseal member thereof being deformed into an open position.

Referring now to FIGS. 8–10, formed on and extending axially from the proximal end 76 of the main body portion 74 is an elongate dilator projection 84. The dilator projection 84 defines a longitudinally extending fluid passage 86 which is in fluid communication with the bore 80 and coaxially aligned therewith. Formed about the outer surface of the dilator projection 84 is a retaining lip 88 which has a generally triangular cross-sectional configuration. Also formed on the proximal end 76 of the main body portion 74 is an annular flange 90 which circumvents the dilator projection 84. As best seen in FIG. 7, the flange 90 is formed on the proximal end 76 in a manner wherein the dilator projection 84 is centrally positioned therewithin. Additionally, as best seen in FIGS. 9 and 10, the flange 90 is formed in a manner defining an arcuately contoured rim which terminates at approximately the distal-most surface of the retaining lip 88.

In addition to the dilator projection 84 and flange 90, formed on the proximal end 76 of the main body portion 74 and extending radially outward therefrom is a stop flange 92. Formed on the proximal surface of the stop flange 92 and extending perpendicularly relative thereto is an opposed pair of identically configured anti-rotation extensions 94. The extensions 94 each have a height substantially equal to that of the flange 90 and extend in generally parallel relation thereto. Extending radially from the peripheral edge of the stop flange 92 in opposed relation is a pair of identically configured stop tabs 96. Formed about and extending radially outward from the outer surface of the main body portion 74 in opposed relation is a pair of leaf springs 98. The leaf springs 98, which are positioned on the main body portion 74 distally from the stop flange 92, are thinly configured to provide the same with resiliency for reasons which will be discussed below. Also formed about and extending radially outward from the outer surface of the main body portion 74 in succession is a pair of identically configured centering flanges 100 which are positioned on the main body portion 74 distally from the leaf springs 98.

In the second embodiment, the housing 72 further comprises a hollow connector cap 102 which is attached to the proximal portion of the main body portion 74. The connector cap 102 includes an annular attachment region 104 formed on the proximal end thereof. The attachment region 104 defines a central opening 106 which communicates with the hollow interior of the connector cap 102. Additionally, formed on the outer surface of the attachment region 104 are Luer threads 108. The attachment of the connector cap 102 to the main body portion 74 is facilitated by the receipt of the stop tabs 96 into an annular channel 110 which is disposed within the inner surface of the connector cap 102 and defines a proximal stop surface 112 and a distal stop surface 114. When the stop tabs 96 are properly received into the channel 110, the extensions 94 formed on the proximal surface thereof are received into complimentary slots 116 which are disposed within the inner surface of the connector cap 102 and extend longitudinally from the proximal stop surface 112 of the channel 110 toward the proximal end of the connector cap 102. As will be discussed in more detail below, the receipt of the extensions 94 into the slots 116 is operable to prevent the rotation of the connector cap 102 relative the main body portion 74.

In addition to the receipt of the stop tabs 96 into the channel 110, the peripheral portions of the leaf springs 98 are received into an annular channel 118 which is also disposed in the inner surface of the connector cap 102 and positioned distally from the channel 110. When the stop tabs 96 and leaf springs 98 are received into the channels 110, 118, the dilator projection 84 extends axially into the central opening 106 of the connector cap 102, but does not protrude from the attachment region 104 thereof. When the connector cap 102 is attached to the main body portion 74 in the aforementioned manner, the centering flanges 100 are adapted to maintain the main body portion 74 centrally within the connector cap 102 such that the dilator projection 84, and in particular the fluid passage 86 thereof, remains coaxially positioned within the central opening 106.

Referring now to FIGS. 7–10, disposed within the central opening 106 of the connector cap 102 and cooperatively engaged to the dilator projection 84 is a reseal member 120 which is fabricated from a resilient material. As best seen in FIGS. 7 and 8, the reseal member 120 comprises a circularly configured proximal portion 122 which defines a top surface 124 and includes a flange 126 formed about the periphery thereof. The reseal member 120 further comprises a cylindrically configured central portion 128 which defines a side surface 130 and a bottom surface 132 having an elongate, generally concave recess 134 formed in the center thereof. Importantly, the recess 134 has a shape complimentary to that of the dilator projection 84 and defines an annular groove 136 within its side wall. In addition to the proximal and central portions 122, 128, the reseal member 120 comprises a tubular distal portion 138 which includes an annular lip 140 formed about the inner surface thereof. Also formed about the inner surface of the distal portion 138 immediately adjacent the bottom surface 132 of the central portion 128 is an annular extension 139. Extending from the top surface 124 of the proximal portion 122 to the apex of the recess 134 is an aperture 142 which is elastically openable and closable. In the injection site 70, the reseal member 120 normally resides in a closed position wherein the aperture 42 is in a closed configuration.

To maintain the aperture 142 in the closed configuration, the distal portion 138 of the reseal member 120 is formed so as to be invertible in relation to the remainder thereof. As best seen in FIG. 7, the distal portion 138, when inverted, is adapted to overlap the side surface 130 of the central portion 128 and apply a radially inward biasing force thereto which maintains the aperture 142 in the closed configuration. Such inversion is accomplished by initially returning the lip 140 outwardly, thus causing the same to extend radially outward with respect to the remainder of the distal portion 138. Thereafter, the distal portion 38 is rolled toward the proximal portion 122, with the lip 140 being inserted into the annular channel 144 defined between the proximal and central portions 122, 128. When the lip 140 is inserted into the channel 144, the extension 139 extends radially outward with respect to the remainder of the reseal member 120. When the distal portion 138 is properly inverted, the reseal member assumes the configuration shown in FIG. 8. For ease of manufacture, the reseal member 120 is molded in the form shown in FIG. 7, with the distal portion 138 thereof being inverted in the aforementioned manner prior to the insertion of the reseal member 120 into the central opening 106 and engagement thereof to the dilator projection 84. As previously explained, due to the resiliency of the material from which the reseal member 120 is fabricated, the inversion of the distal portion 138 facilitates the application of a radially inward biasing force to the central portion 128, thus mainlining the aperture 142 in the closed configuration.

In the injection site 70, the housing 72 further comprises an annular lock ring 146 for securing the reseal member 120 to the connector cap 102, and in particular to the attachment region 104 thereof. The attachment of the reseal member 120 to the connector cap 102 is accomplished by the rigid capture of the flange 126 between the outer surface of the attachment region 104 and lock ring 146 which is itself attached to the connector cap 102 via a sonic bonding process. When attached to the connector cap 102 via the lock ring 146, the central portion 128 of the reseal member 120 (which is covered by the inverted distal portion 138) resides within the central opening 106 and hollow interior of the connector cap 102.

As previously indicated, in addition to being rigidly secured to the connector cap 102, the reseal member 120 is cooperatively engaged to the dilator projection 84. In the injection site 70, such cooperative engagement is achieved by the insertion of the dilator projection 84 into the recess 34 of the reseal member 120. When the dilator projection 84 is fully inserted into the recess 134, the retaining lip 88 formed thereabout is received into the groove 136 disposed within the side wall of the recess 134. When the retaining lip 88 is received into the groove 136, the distal portion of the reseal member 120 is compressed into and thus tightly contained within the annular space defined between the dilator projection 84 and the flange 90, with the extension 139 extending radially outward from the reseal member 120 being abutted against the inner surface of the flange 90 and the distal end of the reseal member 120 being disposed in abutting contact with the proximal end 76 of the main body portion 74. Advantageously, the formation of the proximal rim of the flange 9 with an arcuate contour aids in the insertion of the distal portion of the reseal member 20 into the annular space between the dilator projection 84 and flange 90. The distal portion of the reseal member 120 is maintained in the annular space between the dilator projection 84 and the flange 90 in part by the retaining lip 88 which, when received into the groove 136, prevents the movement of the reseal member 120 proximally relative the dilator projection 84. As will be recognized, the engagement of the reseal member 120 to the dilator projection 84 typically occurs prior to the attachment thereof to the connector cap 102 via the lock ring 146.

The reseal member 120, due to its construction, is deformable such that the application of distally directed pressure thereto will cause it to distally advance within the central opening 106 to an open position wherein the aperture 142 assumes an open configuration (as shown in FIG. 10). Conversely, the removal of the distally directed pressure from the reseal member 120 will cause it to resiliently return to the closed position wherein the aperture 142 assumes the closed configuration (as shown in FIG. 9). In particular, when the reseal member 120 is in the closed position, the top surface 124 of the proximal portion 122 extends over (i.e., covers) the proximal end of the attachment region 104, with the aperture 142 being in the closed configuration due to the radially inward biasing force applied to the central portion 128 by the inverted distal portion 138. When the tip 148 of an introducer device 150 (such as a syringe or Luer connector as shown in FIG. 6) is used to apply distally directed pressure to the top surface 124 of the proximal portion 122, such pressure application causes the reseal member 120 (with the exception of the flange 126) to distally advance within the central opening 106, as shown in FIG. 10.

The advancement of the reseal member 120 distally within the central opening 106 causes the aperture 142 to be forced over the dilator projection 84 in a manner wherein the proximal tip of the dilator projection 84 protrudes from the top surface 124 of the proximal portion 122 and is received into the outlet passage 152 of the introducer device 150. The extension of the dilator projection 84 through the aperture 142 allows fluid to flow from the outlet passage 152 of the introducer device 150 into the bore 80 via the fluid passage 86 of the dilator projection 84. Due to the resiliency of the reseal member 120, its engagement to the dilator projection 84, and its rigid attachment to the attachment region 104, the removal of the introducer device 150 from within the injection site 70 allows it to resiliently return to its closed position, thus causing the aperture 142 to once again assume the closed configuration. In this respect, when no distally directed pressure is applied to the top surface 124 of the proximal portion 122, the aperture 142 is maintained in the closed configuration by the radially inward biasing force exerted on the central portion 128 by the inverted distal portion 138. The tip 148 of the introducer device 150 is preferably sized having an outer diameter dimension which is slightly less than the inner diameter dimension of the central opening 106, thus allowing the stretched region of the proximal portion 122 to form a seal between the outer surface of the tip 148 and the inner surface of the central opening 106.

In the injection site 70, the reseal member 120 is preferably fabricated from silicone, though similar elastic materials such as rubber may be utilized as an alternative. Advantageously, the Luer threads 108 formed on the outer surface of the attachment region 104 allow introducer devices such as Luer connectors to be interfaced to the injection site 70. Additionally, the uniform top surface 124 defined by the proximal portion 122 when the reseal member 120 is in the closed position allows for the quick and easy cleaning and disinfection thereof.

Referring now to FIGS. 9 and 10, the main body portion 74 of the housing 72 normally resides in a first position within the connector cap 102 (as shown in FIG. 9), and is adapted to move distally relative the connector cap 102 to a second position therewithin when distally directed pressure is applied to the reseal member 120 (as shown in FIG. 10). When the distally directed pressure is removed from the reseal member 120, the main body portion 74 is adapted to resiliently return to the first position. In the injection site 70, the main body portion 74 is biased to the first position by the leaf springs 98 which are molded on the outer surface thereof and received into the channel 118 disposed in the inner surface of the connector cap 102. When distally directed pressure is applied to the reseal member 120, and in particular the top surface 124 of the proximal portion 122, the main body portion 74 is moved distally within the interior of the connector cap 102 toward its second position, thus resulting in the flexion of the leaf springs 98. The distal movement of the main body portion 74 within the connector cap 102 is limited by the abutment of the stop tabs 96 against the distal stop surface 114 defined by the channel 110. When such abutment occurs, the main body portion 74 resides in the second position. Importantly, the anti-rotation extensions 94 are sized such that when the stop tabs 96 are abutted against the distal stop surface 114, portions of the extensions 94 remain within their respective slots 116. The distally directed pressure exerted on the top surface 124 of the proximal portion 122 is transmitted to the main body portion 74 via the reseal member 120 which, as previously indicated, is cooperatively engaged to the dilator projection 84 and abutted against the proximal end 76 of the main body portion 74.

When the distally directed pressure is removed from the top surface 124 of the proximal portion 122, the leaf springs 98 returns to their original, unflexed positions which results in the movement of the main body portion 74 proximally within the connector cap 102 toward its first position. The proximal movement of the main body portion 74 within the connector cap 102 is limited by the abutment of the stop tabs 96 against the proximal stop surface 112 defined by the channel 110. When such abutment occurs, the main body portion 74 resides in the first position. Importantly, the length of travel of the main body portion 74 when it moves from the first to the second positions is significantly less than the length of travel of the reseal member 120 when it moves from the closed position to the open position, thus allowing the aperture 142 of the reseal member 120 to be forced over the dilator projection 84 despite the distal movement of the main body portion 74 within the connector cap 102. The return of the main body portion 74 to the first position, though primarily being facilitated by the action of the leaf springs 98, is also aided by the reseal member 120. In this respect, due to the cooperative engagement of the reseal member 120 to the dilator projection 84 as facilitated by the receipt of the retaining lip 88 into the groove 136, the resilient return of the reseal member 120 to the closed position pulls the dilator projection 84, and hence the main body portion 74, proximally toward the proximal end of the connector cap 102.

Though not shown, it will be recognized that alternative means may be employed to provide the radially inwardly biasing force to the central portion 128 of the reseal member 120 to maintain the aperture 142 in the closed configuration. In this respect, the reseal member 120 may be formed without the invertable, tubular distal portion 138, with the radially inwardly biasing force being applied to the central portion 128 via an O-ring which is received into the annular channel 144 defined between the proximal and central portions 122, 128.

Referring now to FIGS. 11–17, illustrated is a needleless injection site 160 constructed in accordance with a third embodiment of the present invention. As will be described in more detail below, the injection site 160 is adapted to be selectively coupled to a Luer connector 162 (as shown in FIGS. 11 and 15), a standard tubular fluid line 164 (as shown in FIGS. 11 and 17), a Y-injection site (as shown in FIG. 16), and a bottle 168 (as shown in FIG. 12). However, it will be recognized that the injection site 160 may additionally be fluidly coupled to various other intravenous infusion components. The injection site 160 comprises a housing 170 which itself comprises an adapter member 172 defining a proximal end 174, a distal end 176 and an interior chamber 178.

Referring now to FIGS. 14–17, the adapter member 172 comprises an upper section 180 which defines the proximal end 174, and a lower section 182 which is rigidly attached to the upper section 180 and defines the distal end 176. The upper and lower sections 180, 182, when attached to each other, define the interior chamber 178. When the upper and lower sections 180, 182 are rigidly attached to each other, the distal portion of the upper section 180 is concentrically positioned within the proximal portion of the lower section 182. Formed on the proximal end 174 of the adapter member 172 is an elongate dilator projection 184 which defines a proximal portion 186 extending axially from the proximal end 174, and a distal portion 188 extending axially into the interior chamber 178. The dilator projection 184 further defines a longitudinally extending fluid passage 190 which is in fluid communication with the interior chamber 178.

Formed about the outer surface of the proximal portion 186 of the dilator projection 184 is a retaining lip 192 which has a generally triangular cross-sectional configuration. The distal portion 188 of the dilator projection 184 preferably has a tapered outer surface for facilitating the connection of the housing 170 to the fluid line 164, as will be described in more detail below. Additionally, the distal end of the distal portion 188 preferably has a beveled configuration defining a piercing tip 194. Formed on the tapered outer surface of the distal portion 188 and extending longitudinally from the proximal end 174 of the adapter member 172 to approximately the halfway point of the distal portion 188 is an elongate rib 189, the use of which will also be discussed below.

In addition to the dilator projection 184, formed on the proximal end 174 of the adapter member 172 and extending radially outward therefrom is a stop flange 196. Formed on the proximal surface of the stop flange 196 and extending perpendicularly relative thereto is an opposed pair of identically configured anti-rotation extensions 198. Additionally, formed about and extending radially outward from the outer surface of the adapter member 172, and in particular the upper section 180 thereof, is a leaf spring 200. The leaf spring 200, which is positioned on the upper section 180 distally from the stop flange 196, is thinly configured to provide the same with resiliency for reasons which will also be discussed below.

In the third embodiment, the housing 170 further comprises a hollow connector cap 202 which is attached to the adapter member 172. The connector cap 202 includes an annular attachment region 204 formed on the proximal end thereof. The attachment region 204 defines a central opening 206 which communicates with the hollow interior of the connector cap 202. Additionally, formed on the outer surface of the attachment region 204 are Luer threads 208. The attachment of the connector cap 202 to the adapter member 172 is facilitated by the receipt of the peripheral portion of the stop flange 196 into an annular channel 210 which is disposed within the inner surface of the connector cap 202 and defines a proximal stop surface 212 and a distal stop surface 214. When the stop flange 196 is properly received into the channel 210, the extensions 198 formed on the proximal surface thereof are received into complimentary slots 216 which are disposed within the inner surface of the connector cap 202 and extend longitudinally from the proximal stop surface 212 of the channel 210 toward the proximal end of the connector cap 202. As will be discussed in more detail below, the receipt of the extensions 198 into the slots 216 is operable to prevent the rotation of the connector cap 202 relative the adapter member 172.

In addition to the receipt of the stop flange 196 into the channel 210, the peripheral portion of the leaf ring 200 is received into an annular channel 218 which is also disposed in the inner surface of the connector cap 202 and positioned distally from the channel 210. When then stop flange 196 and leaf spring 200 are received into the channels 210, 218, the proximal portion 186 of the dilator projection 184 extends axially into the central opening 206 for the connector cap 202, but does not protrude from the attachment region 204 thereof. The lower section 182 of the adapter member 172 is preferably sized having an outer diameter dimension slightly less than the inner diameter dimension of the connector cap 202 for purposes of maintaining the adapter member 172 centrally within the connector cap 202 such that the proximal portion 186 of the dilator projection 184, and in particular the fluid passage 190 thereof, remains coaxially positioned within the central opening 206.

Referring now to FIGS. 13 and 17, disposed within the central opening 206 of the connector cap 202 and cooperatively engaged to the proximal portion 186 of the dilator projection 184 is a reseal member 220 which is fabricated from a resilient material. The reseal member 220 comprises a tubular proximal portion 224 having an extension 226 formed about the outer surface thereof. The reseal member 220 further comprises a cylindrically configured distal portion 228 which defines a top surface 230, bottom surface 232 and side surface 234. Formed in the center of the bottom surface 232 is an elongate, generally concave recess 236 which has a shape complimentary to that of the proximal portion 186 of the dilator projection 184 and defines an annular groove 238 within its side wall. Extending from the top surface 230 of the distal portion 228 to the apex of the recess 236 is an aperture 240 which is elastically openable and closable. In the injection site 160, the reseal member 220 normally resides in a closed position wherein the aperture 240 is in a closed configuration.

To maintain the aperture 240 in the closed configuration, the proximal portion 224 of the reseal member 220 is formed so as to be invertible in relation to the remainder thereof. As best seen in FIG. 13, the proximal portion 224, when inverted, is adapted to overlap the side surface 234 of the distal portion 238 and apply a radially inward biasing force thereto which maintains the aperture 240 in the closed configuration. Such inversion is accomplished by initially rolling the proximal portion 224 toward the distal portion 228, and thereafter turning the extension 226 outwardly so as to cause the same to extend radially outward with respect to the remainder of the reseal member 220. When the proximal portion 224 is properly inverted, the reseal member assumes the configuration shown in FIG. 17. For ease of manufacture, the reseal member 220 is molded in the form shown in FIG. 13, with the proximal portion 224 thereof being inverted in the aforementioned manner prior to the insertion of the reseal member 220 into the central opening 206 and the engagement thereof to the proximal portion 186 of the dilator projection 184. As previously explained, due to the resiliency of the material from which the reseal member 220 is fabricated, the inversion of the proximal portion 224 facilitates the application of a radially inward biasing force to the distal portion 228, thus maintaining the aperture 240 in the closed configuration. When the reseal member 220 is fully inserted into the central opening 206 and cooperatively engaged to the proximal portion 186 of the dilator projection 184, the distal portion 228 of the reseal member 220 (which is covered by the inverted proximal portion 224) resides within the central opening 206 and hollow interior of the connector cap 202. Additionally, the top surface 230 of the reseal member 220, which has a slight arcuate contour, is substantially flush with the proximal end of the attachment region 204.

As previously indicated, the reseal member 220 is cooperatively engaged to the proximal portion 186 of the dilator projection 184. In the injection site 160, such cooperative engagement is achieved by the insertion of the proximal portion 186 into the recess 236 of the reseal member 220. When the proximal portion 186 is fully inserted into the recess 236, the retaining lip 192 formed thereabout is received into the groove 238 disposed within the side wall of the recess 236. When the retaining lip 192 is received into the groove 238, the distal portion of the reseal member 220 is forced between the proximal portion 186 and the extensions 198, with the extension 226 extending radially outward from the reseal member 220 being abutted against the inner surfaces of the extensions 198 and the distal end of the reseal member 220 being disposed in abutting contact with the proximal end 174 of the adapter member 172. The reseal member 220 is tightly held by the proximal portion 186 of the dilator projection 184 and extensions 198 when forced therebetween in the aforementioned manner. The distal portion of the reseal member 220 is maintained between the proximal portion 186 and the extensions 198 in part by the retaining lip 192 which, when received into the groove 238, prevents the movement of the reseal member 220 proximally relative the proximal portion 186.

The reseal member 220, due to its construction, is deformable such that the application of distally directed pressure thereto will cause it to distally advance within the central opening 206 to an open position wherein the aperture 240 assumes an open configuration (as shown in FIGS. 15 and 16). Conversely, the removal of the distally directed pressure from the reseal member 220 will cause it to resiliently return to the closed position wherein the aperture 240 assumes the closed configuration (as shown in FIG. 17). When the reseal member 220 is in the closed position, the top surface 230 thereof is substantially flush with the proximal end of the attachment region 204, with the aperture 240 being in the closed configuration due to the radially inward biasing force applied to the distal portion 228 by the inverted proximal portion 224. When the tip 242 of an introducer device 244 (such as a Luer connector as shown in FIG. 15 and a syringe as shown in FIG. 16) is used to apply distally directed pressure to the top surface 230, such pressure application causes the reseal member 220 to distally advance within the central opening 206, as shown in FIGS. 15 and 16.

The advancement of the reseal member 220 distally within the central opening 206 causes the aperture 240 to be forced over the proximal portion 186 of the dilator projection 184 in a manner wherein the proximal tip of the proximal portion 186 protrudes from the top surface 230 of the distal portion 228 and is received into the outlet passage 246 of the introducer device 244. The extension of the proximal portion 186 through the aperture 240 allows fluid to flow from the outlet passage 246 of the introducer device 244 into and through the fluid passage 190 of the dilator projection 184. Due to the resiliency of the reseal member 220 and its engagement to the dilator projection 184, the removal of the introducer device 244 from within the injection site 160 allows it to resiliently return to its closed position, thus causing the aperture 240 to once again assume the closed configuration. In this respect, when no distally directed pressure is applied to the top surface 230 of the distal portion 238, the aperture 240 is maintained in the closed configuration by the radially inward biasing force exerted on the distal portion 238 by the inverted proximal portion 224.

In the injection site 160, the reseal member 220 is preferably fabricated from silicone, though similar elastic materials such as rubber may be utilized as an alternative. The Luer threads 208 formed on the outer surface of the attachment region 204 allow an introducer device 244 such as the Luer connector shown in FIG. 15 to be maintained in coupled engagement to the injection site 160. Additionally, the uniform top surface 230 defined by the distal portion 228 when the reseal member 220 is in the closed position allows for the quick and easy cleaning and disinfection thereof.

Referring now to FIGS. 15–17, the adapter member 172 of the housing 170 normally resides in a first position within the connector cap 202 (as shown in FIG. 17), and is adapted to move distally relative the connector cap 202 to a second position therewithin when distally directed pressure is applied to the reseal member 220 (as shown in FIGS. 15 and 16). When the distally directed pressure is removed from the reseal member 220, the adapter member 172 is adapted to resiliently return to the first position. In the injection site 160, the adapter member 172 is biased to the first position by the leaf spring 200 which is molded on the outer surface of the upper section 180 thereof and received into the channel 210 disposed in the inner surface of the connecter cap 202. When distally directed pressure is applied to the reseal member 220, and in particular the top surface 230 of the distal portion 228, the adapter member 172 is moved distally within the interior of the connector cap 202 toward its second position, thus resulting in the flexion of the leaf spring 200. The distal movement of the adapter member 172 within the connector cap 202 is limited by the abutment of the peripheral portion of the stop flange 196 against the distal stop surface 214 defined by the channel 210. When such abutment occurs, the adapter member 172 resides in the second position. Importantly, the anti-rotation extensions 198 are sized such that when the stop flange is abutted against the distal stop surface 214, portions of the extensions 198 remain within their respective slots 216. The distally directed pressure exerted on the top surface 230 of the distal portion 228 is transmitted to the adapter member 172 via the reseal member 220 which, as previously indicated, is cooperatively engaged to the proximal portion 186 of the dilator projection 184 and abutted against the proximal end 174 of the adapter member 172.

When the distally directed pressure is removed from the top surface 230 of the distal portion 228, the leaf spring 200 returns to its original, unflexed position which results in the movement of the adapter member 172 proximally within the connector cap 202 toward its first position. The proximal movement of the adapter member 172 within the connector cap 202 is limited by the abutment of the peripheral portion of the stop flange 196 against the proximal stop surface 212 defined by the channel 210. When such abutment occurs, the adapter member 172 resides in the first position. Importantly, the length of travel of the adapter member 172 when it moves from the first to the second positions is significantly less than the length of travel of the reseal member 220 when it moves from the closed position to the open position, thus allowing the aperture 240 of the reseal member 220 to be forced over the proximal portion 186 of the dilator projection 184 despite the distal movement of the adapter member 172 within the connector cap 202. Additionally, the anti-rotation extensions 198 are positioned on the proximal surface of the stop flange 196 so as to be longitudinally movable within the slots 216 yet prevent the extension 226 of the reseal member 220 which is abutted against the inner surfaces thereof from contacting the inner surface of the connector cap 202. The return of the adapter member 172 to the first position, though primarily being facilitated by the action of the leaf spring 200, is also aided by the reseal member 220. In this respect, due to the cooperative engagement of the reseal member 220 to the proximal portion 186 of the dilator projection 184 as facilitated by the receipt of the retaining lip 192 into the groove 238, the resilient return of the reseal member 220 to the closed position pulls the dilator projection 184, and hence the adapter member 172, proximally toward the proximal end of the connector cap 202.

Referring now to FIGS. 14 and 17, defined within the distal end 176 of the adapter member 172, and in particular the lower section 182 thereof, is a lock region for facilitating the connection of the injection site 160 to an infusion component such as the Luer connector 162, Y-injection site 166 and bottle 168. The lock region of the adapter member 172 preferably comprises three sets of Luer thread pitch barbs 248 which are formed on the inner surface of the lower section 182 in equidistantly spaced intervals of approximately 120°. Each set of pitch barbs 248 extends longitudinally from the distal end 176 of the adapter member 172 into the interior chamber 178, and terminates at approximately the distal end of the upper section 180. As best seen in FIG. 17, each set of pitch barbs 248 is formed within the lower section 182 so as to be oriented radially inward from the inner surface thereof.

As previously explained, the adapter member 172 of the housing 170 is comprised of the upper and lower sections 180, 182 which are rigidly attached to each other. In the third embodiment, the lower section 182 of the adapter member 172 is molded to include a cover member 250 which is attached to one of the sets of pitch barbs 248 via a tang 252. The cover member 250 defines a tapered bore which is complimentary to the tapered outer surface of the distal portion 188 of the dilator projection 184. In this respect, subsequent to the assembly of the injection site 160 in the aforementioned manner, the tang 252 is manually broken, thus allowing the cover member 250 to be slidably advanced over the distal portion 188 of the dilator projection 184. Due to the bore of the cover member 250 and the distal portion 188 having mutually tapered configurations, the cover member 250 is frictionally maintained upon the distal portion 188 subsequent to being slidably advanced over the same. Advantageously, the cover member 250 prevents any inadvertent contamination of the distal portion 188 prior to the incorporation of the injection site 160 into an intravenous infusion assembly. The cover member 250 also prevents a user from being inadvertently injured by the piercing tip 194 of the distal portion 188.

In addition to the lower section 182 being molded with the cover member 250, the connector cap 202 of the injection site 160 is molded to include a tubular adapter sleeve 254 which is attached to the proximal end of the attachment region 204 via three (3) equidistantly spaced tangs 256. The adapter sleeve 254 has a tapered outer surface 257 and includes a tapered bore 258 extending longitudinally therethrough which, like the bore of the cover member 250, is complimentary to the tapered outer surface of the distal portion 188 of the dilator projection 184. Disposed within the side wall of the bore 258 are a plurality of equidistantly spaced slots 260 which extend longitudinally from the end of the adapter sleeve 254 of greater diameter to a depth approximately commensurate with a shoulder 262 defined within the outer surface 257. As will be discussed in more detail below, the adapter sleeve 254 is used to facilitate the attachment of the injection site 160 to the Luer connector 162. As will be recognized, the cover member 250 is necessarily removed from the lower section 182 (or from upon the distal portion 188) and the adapter sleeve 254 removed from the connector cap 202 prior to the utilization of the injection site 160.

As previously indicated, the injection site 160 is adapted to be engaged to the Luer connector 162, fluid line 164, Y-injection site 166 and bottle 168. As seen in FIG. 15, the engagement of the injection site 160 to the Luer connector 162 is accomplished by slidably advancing the adapter sleeve 254 over the distal portion 188 of the dilator projection 184 subsequent to the removal of the cover member 250 therefrom and the detachment of the adapter sleeve 254 from the connector cap 202. Since the outer surface of the distal portion 188 and the bore 258 of the adapter sleeve 254 have mutually tapered configurations, the adapter sleeve 254 is frictionally maintained upon the distal portion 188 subsequent to being slidably advanced over the same. Importantly, each of the slots 260 is sized and configured to slidably receive the rib 189 formed on the outer surface of the distal portion 188, with the advancement of the adapter sleeve 254 proximally along the distal portion 188 being limited by the abutment of the distal end of the rib 189 against the closed end of the slot 260 into which it is received. Advantageously, the receipt of the rib 189 into the slot 260 is operable to prevent the rotation of the adapter sleeve 254 upon the distal portion 188 of the dilator projection 184.

Subsequent to the attachment of the adapter sleeve 254 to the distal portion 188 in the aforementioned manner, the adapter sleeve 254 is slidably inserted into the lumen of the Luer connector 162. The advancement of the adapter sleeve 254 into the lumen of the Luer connector 162 is continued until such time as the Luer threads formed on the outer surface of the Luer connector 162 are engaged by the pitch barbs 248 of the lock region. Due to the tapered outer surface 257 of the adapter sleeve 254, the same is frictionally maintained within the lumen of the Luer connector 162 subsequent to being inserted thereinto. Additionally, the Luer connector 162 is prevented from being pulled distally away from the adapter member 172, and in particular the adapter sleeve 254, by the engagement of the pitch barbs 248 to the Luer threads thereof. As such, the combination of the frictional retention of the adapter sleeve 254 within the lumen and the engagement of the pitch barbs 248 to the Luer threads creates a secure interface between the injection site 160 and the Luer connector 162. When the reseal member 220 is moved to the open position, fluid flows from the outlet passage 246 of the introducer device 244 into the lumen of the Luer connector 162 via the fluid passage 190 of the dilator projection 184 and bore 258 of the adapter sleeve 254.

Referring now to FIG. 16, the engagement of the injection site 160 to the Y-injection site 166 is accomplished by initially removing the cover member 250 from the distal portion 188 of the dilator projection 184, and removing the adapter sleeve 254 from the connector cap 202. Thereafter, the injection site 160, and in particular the adapter member 172 thereof, is advanced over the top end of the Y-injection site 166 in a manner wherein the distal portion 188 of the dilator projection 184 is extended into the Y-injection site 166 (with any diaphragm attached to the top end thereof being pierced by the piercing tip 194 of the distal portion 188). In addition to the distal portion 188 of the dilator projection 184 being extended into the Y-injection site 166, the enlarged end region of the Y-injection site 166 is captured within the pitch barbs 248, thus preventing the movement thereof distally away from the adapter member 172 and removal of the distal portion 188 from therewithin. When the reseal member 220 is moved to the open position, fluid flows from the outlet passage 246 of the introducer device 244 into the Y-injection site 166 via the fluid passage 190 of the dilator projection 184. Though not shown in detail, the engagement of the injection site 160 to the neck of the bottle 168 occurs in the same manner as described in relation to the Y-injection site 166.

As seen in FIG. 17, the engagement of the injection site 160 to the tubular fluid line 164 is accomplished by initially removing the cover member 250 from the distal portion 188 of the dilator projection 184, and removing the adapter sleeve 254 from the connector cap 202. Thereafter, the distal portion 188 of the dilator projection 184 is slidably advanced into the lumen of the fluid line 164. Due to the tapered outer surface of the distal portion 188, the same is frictionally maintained within the fluid line 164 subsequent to being inserted into the lumen thereof. When the reseal member 220 is moved to the open position, fluid flows from the introducer device into the fluid line 164 via the fluid passage 190 of the dilator projection 184.

Additional modifications and improvements of the present invention may also be apparent to those skilled in the art. Thus, the particular combination of parts described and illustrated herein is intended to represent only certain embodiments of the present invention, and is not intended to serve as limitations of alternative devices within the spirit and scope of the invention.

What is claimed is:

1. A needleless injection site, comprising:
    a housing;
    a reseal member attached to the housing, said reseal member having an elastically openable and closable aperture formed therein and normally residing in a closed position wherein the aperture is in a closed configuration;
    said reseal member being deformable such that the application of distally directed pressure thereto will cause the aperture to assume an open configuration, and the removal of the distally directed pressure therefrom will allow the aperture to return to the closed configuration;
    a flange formed about the periphery of the reseal member;
    a central portion; and
    a distal portion, said distal portion being invertible and adapted to overlap the central portion and apply a radially inward biasing force thereto when inverted which maintains the aperture in the closed configuration when no distally directed pressure is applied to the reseal member.

2. The injection site of claim 1 further comprising a lock ring for securing the reseal member to the housing, said flange being rigidly captured between said housing and said lock ring.

* * * * *